United States Patent
White et al.

(10) Patent No.: US 8,123,922 B2
(45) Date of Patent: Feb. 28, 2012

(54) NANOPORE BASED ION-SELECTIVE ELECTRODES

(75) Inventors: Henry S. White, Salt Lake City, UT (US); Ryan J. White, Santa Barbara, CA (US); Richard B. Brown, Salt Lake City, UT (US); Hakhyun Nam, Seoul (KR); Jun Ho Shim, Seoul (KR)

(73) Assignee: University of Utah Research Foundation, Salt Lake City, UT (US)

( * ) Notice: Subject to any disclaimer, the term of this patent is extended or adjusted under 35 U.S.C. 154(b) by 1208 days.

(21) Appl. No.: 11/852,061

(22) Filed: Sep. 7, 2007

(65) Prior Publication Data

US 2010/0038243 A1   Feb. 18, 2010

Related U.S. Application Data

(60) Provisional application No. 60/842,904, filed on Sep. 7, 2006.

(51) Int. Cl.
*G01N 27/333* (2006.01)
(52) U.S. Cl. ...................................................... 204/416
(58) Field of Classification Search .......... 204/416–420; 205/789, 789.5
See application file for complete search history.

(56) References Cited

U.S. PATENT DOCUMENTS

| 4,721,601 A | 1/1988 | Wrighton et al. |
| 4,874,499 A | 10/1989 | Smith et al. |
| 4,874,500 A | 10/1989 | Madou et al. |
| 4,929,313 A | 5/1990 | Wrighton |
| 5,066,582 A | 11/1991 | Tsuruta et al. |

OTHER PUBLICATIONS

Uhlig et al. "Miniaturized Ion-Selective Chip Electrode for Sensor Application," Anal. Chem. 1997, 69, 4032-4038.*
Akashi et al., "Deep reactive ion etching of borosilicate glass using an anodically bonded silicon wafer as an etching mask," J. Micromech. Microeng. 16 (2006) 1051-1056 published Apr. 7, 2006.*
Li et al., "Conical Nanopore Membranes. Preparation and Transport Properties," Anal. Chem. 2004, 76, 2025-2030.*
Wang et al, "Electrostatic-Gated Transport in Chemically Modified Glass Nanopore Electrodes," In: J. Am. Chem. Soc., May 19, 2006, 128, pp. 7679-7686, Abstract; p. 7681, para1 and 3-5: p. 7682, para 2.

* cited by examiner

*Primary Examiner* — Alex Noguerola
(74) *Attorney, Agent, or Firm* — Thorpe North & Western LLP

(57) ABSTRACT

Nanopore based ion-selective electrodes and methods of their manufacture as well as methods for their use are disclosed and described. The nanopore based ion-selective electrode can include a pore being present in a solid material and having a nanosize opening in the solid material, a metal conductor disposed inside the pore opposite the opening in the solid material, a reference electrode material contacting said metal conductor and disposed inside the pore, a conductive composition in contact with the reference electrode and disposed in the pore, and an ion-selective membrane. The ion-selective membrane can be configured to isolate the metal conductor, reference electrode material, and conductive composition together within the pore.

25 Claims, 11 Drawing Sheets

NANOPORE BASED ION-SELECTIVE ELECTRODES

RELATED APPLICATIONS

This application claims the benefit of U.S. Provisional Application No. 60/842,904, filed Sep. 7, 2006, which is incorporated herein by reference.

GOVERNMENT INTEREST

The research underlying the present invention was supported in part by the Defense Advanced Research Project Agency, Grant #FA9550-06-C-0060 and the National Science Foundation, Grant #BES0529385. The U.S. government may have certain rights in this invention.

FIELD OF THE INVENTION

The invention relates to the field of nanotechnology, particularly to nanopore based ion-selective electrodes and methods of making and using such nanopore based ion-selective electrodes in chemical, biochemical, and gas sensing.

BACKGROUND

As advances in science increasingly demand the measurement of chemical species or reactions in microscale domains, fundamental and applied studies on various types of ultramicroelectrodes (UMEs) have attracted considerable attention. Voltammetric UMEs (disks, rings, or conical tip electrodes of micro- or submicrometer dimension) have been widely used to study the release of neurotransmitters from a single cell, rapid homogeneous or heterogeneous electron-transfer kinetics, and electrochemical reactions in poorly conducting media and applied as tips in high-resolution scanning electrochemical microscopy (SECM). Potentiometric UMEs, comprising simple metal wires, metal wires coated with insoluble salt (e.g., Ag/AgCl), or conventional ion-selective electrodes (ISEs) fabricated in micropipets, have also been developed to investigate the in vivo ionic activity of single cells and, more recently, as a probe of SECM. However, the application of potentiometric UMEs for SECM studies is rather limited in practice, in part due to the complexity of constructing such system.

Several types of potentiometric UMEs are found in the literature. Ag/AgCl microelectrode disks (10- and 50-µm diameter) were used to probe the diffusion of Ag+ on a planar Ag electrode and to measure ion flux of Cl⁻ over polyaniline films electrodeposited on Pt. Antimony-based pH microdisk electrodes (tip size, ~3-µm diameter) were also fabricated and used to image the local pH changes in several model chemical systems, e.g., reduction of water on Pt electrode, the corrosion of AgI in aqueous potassium cyanide, enzyme reactions of immobilized urease, and metabolic activity of yeast cells. Neutral carrier-based micropipet ISEs (typical tip diameter, 1-20 µm) were used as probes in SECM to image local concentration profiles of $NH_4^+$, $K^+$, and $Zn^{2+}$ ions.

Previous studies suggest that the fabrication of potentiometric UMEs requires a substantial effort in preparing submicrometer-sized electrode tips or in the construction of micropipet-based ion-selective electrodes. Ion-selective metal oxide layers (e.g., iridium oxide, silver/silver chloride, etc.) may be deposited at the exposed end of the submicrometer-sized electrode tip or the tip coated with ionophore-doped solvent polymeric membranes to result in a desired ion selectivity. However, the affixed layer on a small electrode area may not be stable even for a short period of time. Therefore, despite some advances there still remains the need for improved electrode designs.

SUMMARY OF INVENTION

Glass nanopore electrodes are a three-dimensional structure for preparing mechanically robust ISEs down to nanoscale dimensions. The fabrication and electrochemical behavior of conical-shaped glass nanopore electrodes can be described as a platform for investigating molecular transport through orifices of nanoscale dimensions and, upon surface chemical modification, as sensors. Cone-shaped glass nanopore structures are ideal for containing additional functional layers, such as ion-selective membranes. The fabrication and application of glass nanopore-based all-solid-state ion-selective electrodes would represent a major advance in the field of ion selective electrochemistry. The depositions of Ag/AgCl (for chloride-selective electrodes), $IrO_2$ (for pH electrodes), and polymer membranes doped with neutral carriers (for $K^+$-selective electrodes) inside the glass nanopore are made possible by this approach.

The present invention provides nanopore based ion-selective electrodes, methods of their manufacture as well as methods for their use. The nanopore based ion-selective electrode can include a pore being present in a solid material and having a nanosize opening in the solid material. A metal conductor can be disposed inside the pore opposite the opening in the solid material. A reference electrode material can be oriented contacting the metal conductor and disposed inside the pore. A conductive composition can be oriented in contact with the reference electrode and disposed in the pore. An ion-selective membrane can be configured to isolate the metal conductor, reference electrode material, and conductive composition together within the pore.

In another embodiment, an ion-selective electrochemical sensor is provided which includes at least one nanopore based ion-selective electrode as described above and a processing unit for processing information from the ion-selective electrode.

In a further embodiment, a process for producing a glass nanopore-based all-solid-state ion-selective electrode (ISE) is provided. The process includes sealing a conductive metal wire in glass or quartz. A disk of the conductive metal wire can be exposed by gentle grinding and etching to form a pore orifice of submicrometer dimension, and as small as a few nanometers. The exposed disk of the conductive metal can be electroplated in the pore with Ag to form a layer of silver on the exposed disk. Further, at least a portion of the Ag layer can be chloridated in order to obtain a AgCl/Ag layer within the pore.

A greater understanding of the present invention may be had from reference to the following detailed description and the appended claims.

BRIEF DESCRIPTION OF THE FIGURES

FIG. 2a shows a conical shaped nanopore electrode with a platinum metal conductor; FIG. 2b shows the electrode of FIG. 2a further including a $IrO_2$-deposited layer; FIG. 2c shows the electrode of FIG. 2a further including a Ag/AgCl deposited layer; FIG. 2d shows the electrode of FIG. 2c further including a hydrogel layer and a polymer membrane-layer.

DETAILED DESCRIPTION OF THE INVENTION

Figure 1:
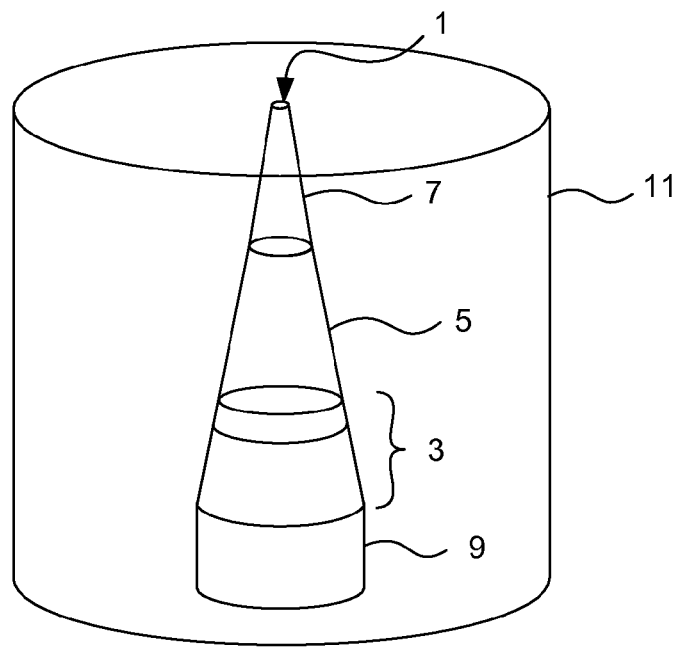
FIG. 1 shows a schematic depiction of a prototypical conical shape ion selective electrode.

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

In describing and claiming the present invention, the following terminology will be used in accordance with the definitions set forth below.

As used herein, the singular forms of "a," "an," and "the" include plural referents unless the context clearly dictates otherwise. Thus, for example, reference to "a reference electrode material" includes one or more of such materials, reference to "a sensor" includes reference to one or more of such devices.

As used herein, the term "solid material" refers to a generally non-porous and non-conductive or isolative material into which a pore can be formed. Further, any non-uniformities or porosity in the solid material are insufficient to disrupt functioning of the electrode.

As used herein, the term "nanosize" when used to describe pore openings refers to openings having a diameter of from about 5 nm to about 1000 nm. However, in some embodiments nanosized pore openings more generally refer to openings of less than about 100 nm.

As used herein, the term "pore" refers to a void volume. Although pores are typically conical or cylindrical in shape, other three dimensional shapes can be useful such as spherical, box shape, etc., as long as the nanosized opening is present.

As used herein, the term "opposite" when referring to placement of features refers to an orientation which is not adjacent. For example, the conductor being opposite the pore opening does not necessarily indicate symmetric placement within the pore. Thus, when opposite, the conductor could be oriented within the pore in any position which allows for a potential across the reference electrode.

As used herein, "microdisk" refers to an exposed region of an electrical conductor (e.g., a metal, semiconductor, oxide, carbon, or polymer) that can be found within a pore. The electrical conductor can be a wire that is embedded in the solid material. When the pore is formed in the solid material and exposes a region of the metal conducting wire the exposed region can be referred to as a microdisk. The exposed region of the metal or electrical conductor may have a geometry different from that of a microdisk.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

As mentioned above, the present invention provides nanopore based ion-selective electrodes and associated methods of manufacture and use. In one embodiment, a nanopore based ion-selective electrode is provided. The nanopore based ion-selective electrode can include a pore being present in a solid material and having a nanosize opening in the solid material. A metal conductor can be disposed inside the pore opposite the opening in the solid material. In addition, a reference electrode material can be oriented contacting the metal conductor and disposed inside the pore. A conductive composition can be in contact with the reference electrode and disposed in the pore. Further, an ion-selective membrane can be oriented and configured to isolate the metal conductor, reference electrode material, and conductive composition together within the pore. The device may be employed as a sensor for detection of chemical and biological species, including ions, molecules and dissolved gases, by measuring the potential between the internal reference electrode and a suitable external reference electrode. FIG. 1 illustrates a prototypical conical shaped ion selective electrode depicting a nanopore 1, reference electrode 3, and other components (e.g., hydrogel 5, ion selective membrane 7, electrical conductor 9, and solid support matrix 11) typically found in an ion selective electrode in accordance with an embodiment of the present invention.

The devices of the present invention can be suitably used singly or in combinations of a plurality of sensors, e.g. as an array. For example, an ion-selective electrochemical sensor can be provided which includes at least one nanopore based ion-selective electrode as described above and an operatively connected processing unit for processing information from the ion-selective electrode. In order to identify and/or measure concentrations of distinct ions, the ion-selective electrochemical sensor can be configured to include an array of two or more nanopore electrodes. For example, a plurality of nanopore sensors can be produced, each having a different semi-permeable membrane and other materials which are optimized for a specific ion.

The nanopore based ion-selective electrodes of the present invention can be formed using a variety of suitable processes and various materials. Exemplary processes for producing a nanopore based all-solid-state ion-selective electrode (ISE) are described in more detail below.

The nanopore ISEs of the present invention are generally formed having a solid material as a support matrix or encapsulating structure for the functional layers within. The solid material in which the nanopore based ion-selective electrodes are formed can be made of any non-porous, non-conductive, or insulating material which acts to support and protect the various functional layers of the device. Examples of such materials include, but are not limited to, glass, polymer, quartz, oxides, other known insulator compositions, or combinations thereof. In one aspect of the present invention, the solid material can comprise or consist essentially of an inorganic material such as glass, quartz or metal oxide. Alternatively, polymer materials can be inexpensive. The solid material can be formed by a suitable deposition process or provided as an existing layer. For example, a glass or quartz support matrix can be formed by a simple bench-top method. An electrochemically sharpened Au or Pt micro-wire is first sealed into a glass or quartz capillary, followed by polishing the glass or quartz until a nanometer-sized metal disk is exposed. The glass nanopore electrode is then fabricated by etching the metal nanodisk electrode to create a pore in glass, with the remaining metal disk comprising the pore base.

A suitable nanopore can be formed in the solid material. Such nanopores can be formed by forming the solid material as a support matrix around a mold which is then partially removed (i.e. an additive process) or forming the nanopore into an existing solid material (i.e. a subtractive process). For example, the pores can be etched or ground into the solid material in order to form a pore. Non-limiting examples of suitable processes for forming the nanopore can include chemical etching, laser ablation, nanolithography, focused ion/electron beam drilling, and the like. Alternatively, the solid material can be sealed around a mold having the desired pore volume dimensions. For example, the solid material can be deposited around a conically shaped mold, e.g. a nanosharpened metal wire. A quartz or glass or other similar solid material may also be molten or heated, e.g. using a $CO_2$ laser, and the sharpened wire inserted therein and allowed to cool around the wire. Any excess material can be gently removed sufficient to expose a portion of the mold. The exposed portion of the mold can generally correspond to a desired pore opening dimension. The exposed portion of the mold can then be removed by chemical etching or other suitable treatments to leave an open pore volume. If the mold is formed of a conductive material, the etching or removal can be ceased at a point corresponding to the desired electrode depth. The remaining portion of the mold can then serve as an electrical interconnect for the nanopore ISE device.

Figure 2A:
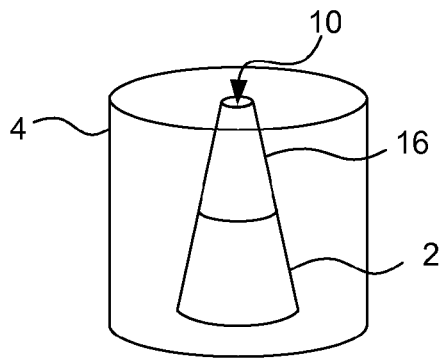
FIGS. 2a through 2d show four schematics depicting intermediate and final structures obtained during the fabrication of nanopore ion-selective electrodes, in accordance with various embodiments of the present invention.

In order to be effective for use with the nanopore based ion-selective electrodes of the present invention, the pores formed in the solid material should have nanosize openings or orifices having diameters of from about 5 nm to about 5000 nm. In one embodiment, the nanosize openings can have a diameter of from 5 nm to about 500 nm. In another embodiment, the pore's nanosize opening can have a diameter of from about 5 nm to about 200 nm. FIG. 2a shows a schematic of an etched solid material 4 having a nanosize pore opening 10 and a platinum metal conductor 2 located inside the conically shaped pore 16 in accordance with an additive process for forming the nanopore.

A conical nanopore structure provides a mechanically robust volume for containing the components of an ion-selective electrode. Specifically, the reference electrode, internal filling solutions (such as gels, hydrogels, and polymers), and ion-selective membrane are protected from external environment such as an external solution to be tested, providing for an exceptionally stable and miniaturized ion-selective electrode. FIG. 1 shows these elements and the manner that they are isolated from the external solution or environment. At the same time, because of the radial convergent flux of ions in the conical geometry, the pore shape provides a low resistance pathway between internal and external reference electrodes for operation of the device. The pored-based ISE is not limited to conical shaped pores. Any geometry that provides low ion transport resistance, mechanical robustness, and a low pore opening to volume ratio can be useful. The small size and robustness of the device lends itself to solid-state ion-selective electrodes (ISEs) and have been demonstrated as useful chemical sensors in model bench-top experiments. In one embodiment, the diameter of the nanosize opening to pore volume ratio can be from about 1:10 (nm:μl) to about 1:100,000 (nm:μl), and preferably from about 1:100 (nm:μl) to about 1:10,000. This ratio can be optimized depending on the thickness and chemical and physical properties of the internal electrode components and is not limited to the examples presented below. Similarly, as a general rule, the depth of the nanopore (to the electrical conductor) can range from about 100 nm to about 100 μm, although other dimensions may be suitable.

The electrical conductor of the nanopore based ion-selective electrodes can generally comprise any conductive material or composite material. Non-limiting examples of such materials include platinum, copper, silver, gold, tin, lead, and alloys thereof. Alternatively, the conductive material can be a conductive polymer. In one aspect of the present invention, the conductors can be incorporated in the solid material of the nanopore ion-selective electrodes in the form of embedded wires. When the pores are created in solid materials containing embedded metal conductor wires the exposed portion of the wire within the pore volume can be referred to as a microdisk. In one embodiment, the metal conductor can be made of platinum, such as a platinum wire. The metal conductor can be present in the pore as a platinum (Pt) microdisk, but is not limited to a disk geometry. For instance, the exposed portion of the conductor could also be conical shape, irregular, or have a rectangular geometry.

The electrical conductor material can be formed as discussed above, i.e. used as a mold which is then partially etched away to leave the pore volume. However, the electrical conductor material can also be formed in a number of other alternative approaches. For example, the entire device may be formed by a layered additive deposition process such as nanolithography, sequential deposition-etch cycles, or the like. As such the conductive material can be sequentially deposited along with the surrounding support matrix, or deposited within the pore after formation thereof.

The exposed surface of the electrical conductor material in the pore can be layered with a suitable reference electrode material. The reference electrode used in the nanopore based ion-selective electrodes can be made of any material known in the art for such purposes. Non-limiting examples of suitable reference electrode materials can include, Ag/AgCl, $IrO_x$, saturated calomel, Cu/Cu ion, metal oxides, conducting polymers, or the like. However, in one embodiment, the reference electrode can be selected from Ag/AgCl or $IrO_x$. Suitable reference electrode materials can be any which are a reversible redox system having a well defined potential (i.e. stable over time) and which can be deposited within the dimensions of the present invention. Although dimensions may vary, the reference electrode layer of the present invention can range from about 5 nm to about 10 µm in thickness, and often from about 50 nm to about 1 µm.

Figure 2B:
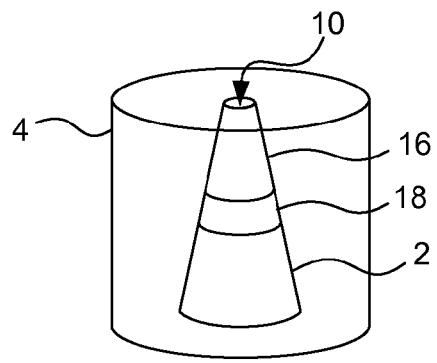
Figure 2C:
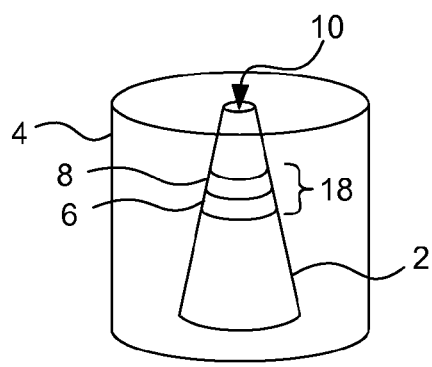

As shown in FIG. 2b, the reference electrode 18 can be electrolytically deposited onto, or placed in contact with, the metal conductor 2. FIG. 2b shows an ion-selective electrode having a reference electrode that comprises a silver layer 6 and a silver chloride layer 8. The silver chloride layer 8 can be formed by chlorinating the silver layer 6 using any chlorination method known in the art such as, but not limited to, electrochemical oxidation of the Ag in presence of $Cl^-$, exposure to a ferric chloride solution, or the like. FIG. 2c shows an ion-selective electrode having a reference electrode 18 comprising $IrO_x$. In one embodiment, x can equal 2, although x can also be 1, 1.5 or 3 as long as the redox chemistry is maintained. The reference electrode can be optionally formed using electrodeposition, atomic layer deposition, chemical vapor deposition, sputtering, or the like.

Figure 2D:
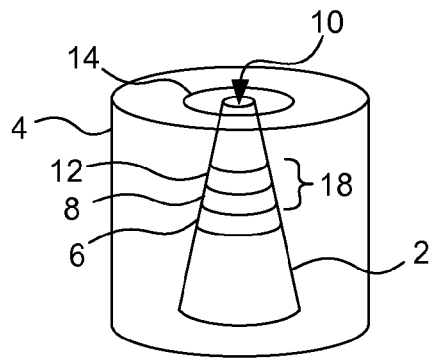

An ionically conductive composition layer can be placed adjacent the reference electrode layer. This layer can be formed of any material which provides ionic conduction between the internal reference electrode and external solution. This layer also generally contains ions or additives that stabilize the internal reference electrode. Non-limiting examples of suitable materials for use in the conductive composition layer can comprise electrolytic solutions (e.g., KCl solutions), conductive hydrogel layers, or another ionically conductive component. In one specific embodiment, the conduction composition layer can comprise a hydrogel such as, but not limited to, polyvinylalcohol dissolved in 0.01 KCl. FIG. 2d shows a nanopore based ion-selective electrode that includes a hydrogel layer 12 as the conductive composition.

Particularly attention must be given to the pH and ionic composition of the conductive composition in order to produce a stable internal reference electrode. As such, in one aspect of the process of producing the nanopore the process can include a step of adjusting an ion concentration, particularly the $Cl^-$ concentration, in the conductive composition sufficient to minimize the solubility of the AgCl layer. When using other internal reference electrodes, e.g., $IrO_x$, the solution may or may not be buffered to control the pH in order to maintain a constant internal reference electrode potential.

The chemical dissolution of the AgCl layer must be considered when constructing a stable nano-reference Ag/AgCl electrode inside the nanopore. While AgCl is very insoluble, $Cl^-$ will form numerous soluble complexes with AgCl, including $AgCl_2^-$ and $AgCl_3$ at $Cl^-$ concentrations greater than 3 mM NaCl. In agreement with the reported solubility of these complexes, we found that ~100 fg quantities of AgCl deposited on the bottom of the glass nanopore electrode quickly dissolved in 1M KCl solutions. In one embodiment, to alleviate this problem, the solution to which the electrode was exposed is presaturated with AgCl and a lower concentration of KCl was employed. In a 3 mM NaCl solution saturated with AgCl, the nano-reference electrode potential was stable is much more stable than in a 1 M KCl.

As shown in FIG. 2d, the conductive composition is placed in contact with the reference electrode on one side and an ion-selective membrane opposite the reference electrode. The conductive composition layer can be formed using any suitable technique. For example, a hydrogel conductive layer can be formed by conventional solution polymerization. The hydrogel can be introduced into the nanopore by capillary action, or by microsyringe methods. Difficulties are encountered in removing trapped air in the nanopore, which is nonconductive and prevents proper operation of the device. The entire electrode can be placed in a solution under reduced pressure (e.g. less than atmospheric) to draw the air out of the nanopore. The conductive composition layer can vary in thickness, though as a general rule, thickness can range from about 100 nm to about 20 µm, although other dimensions may be suitable.

An ion-selective membrane can be deposited between the conductive composition layer and an external fluid to be tested. Any ion-selective membrane known in the art can be used in the ion-selective electrodes of the present invention. Examples of ion-selective membranes include by are not limited to ion-selective polymers, membrane, oxide film, monolayer, or other ion-selective suitable coatings. One skilled in the art could readily determine which membrane to use based on the desired ion selectivity. However, non-limiting examples of suitable ion-selective membranes can include polymer or ceramics and more specifically PVA-based membranes having a suitable ion channel or carrier such as valinomycin. For instance, a very useful ion-selective membrane for $Ca^{2+}$ nanopore ion selective electrode is 5% N,N,N',N'-tetra[cyclohexyl]diglycolic acid diamide, 10% carboxylated PVC, and 85% Bis(2-ethylhexyl)adipate.

In one aspect, the ion-selective membranes can be positioned or deposited at or across the pore nanosize opening of the ion-selective electrodes. In another aspect of the invention, the ion-selective membrane can be positioned in contact with the conductive composition so as to form a barrier between the conductive composition and materials external to the pore. The ion-selective material can be ionically conductive and be capable of selective transporting or adsorbing the intended analyte ion or polyion in the external solution. The membrane can be deposited by capillary active from a solution containing the membrane components or introduced by microsyringe techniques. Other types of self-assembling membranes can be deposited, such as by painting a lipid solution across the orifice and allowing for the spontaneous formation of a thin lipid bilayer. As a general guideline, the membrane can have a thickness ranging from about 80 nm to about 25 µm, and in some cases from about 200 nm to about 2 µm.

The invention is further described with the aid of the following illustrative non-limiting examples.

EXAMPLES

Example 1

Overview of the Fabrication of Nanopore Electrode

The fabrication of glass nanopore electrodes begins when a Pt wire with a sharpened tip was sealed in a soda lime glass capillary, and the glass was polished to expose a Pt nanodisk electrode. The exposed Pt surface was then electrochemically etched in a 1.2 M $CaCl_2$ solution to create a conical pore within the glass, with a Pt microdisk embedded at the bottom of the pore. The radius of the orifice of the nanopore electrodes prepared as described here was normally less than 1.0 µpm. The final structure of the electrode is schematically depicted in FIGS. 1 and 2a.

Example 2

Deposition of $IrO_2$ Film in the Glass Nanopore Electrode

Electrodeposition of iridium oxide film on a nanopore electrode was performed by cycling the applied potentials from 1.2 V to −0.85 V (vs. Ag/AgCl) one to three times at a scan rate of 100 mV/s in a fresh deposition solution. The deposition solution was prepared as follows. A 75 mg of $IrCl_4$ was dissolved in 50 mL of water, and magnetically stirred for 30 min. A 0.5 mL aliquot of 30% hydrogen peroxide solution was added and stirred for 10 min. A 250 mg of oxalic acid dehydrate was added and the solution was stirred again for 10 more min. The pH of the solution was adjusted slowly to 10.5 by adding small portions of anhydrous potassium carbonate. The resulting yellow solution was covered and left at room temperature for 2 days for stabilization. About 2 mL of fresh deposition solution was used for the preparation of each electrode. Once the deposition is complete, the nanopore electrode tip was washed with distilled water and air-dried. The final structure of the electrode is schematically depicted in FIG. 2c.

Example 3

Deposition of Ag/AgCl Film in the Glass Nanopore Electrode

The electrodeposition of Ag at the Pt electrode in the nanopore was performed by cycling the applied potential from 0.0 V to −0.15 V (vs. Ag/AgCl) once at the scan rate of 1.0 mV/s in a fresh deposition solution. The deposition solution was prepared to contain 0.1 M $AgNO_3$, 0.2 M EDTA, 0.5 M $NH_4OH$, and 0.1 M $NH_4NO_3$. Once the deposition is complete, the nanopore electrode is washed with distilled water and air dried. The AgCl layer was formed by chloridating the electrodeposited Ag surface with a 3 M $FeCl_3$ solution for 30 min. The final structure of the electrode is schematically depicted in FIG. 2b.

Example 4

Preparation of a Polymer Membrane-Filled Nanopore Electrode

Cocktails of polymer membranes were prepared by dissolving varying proportions of c-PVC, plasticizer (DOA), lipophilic additives (KTFPB and ETH500), neutral carrier (valinomycin) in THF; the detailed compositions are listed in Tables 1 and 2. The hydrogel solution was prepared by dissolving 4 wt % of PVA in $10^{-2}$ M KCl solution. The membrane cocktails and hydrogel were dispensed onto the Ag/AgCl− deposited Pt nanopore electrode using a syringe pump (Harvard Apparatus model PHD 22/2000, Holliston, Mass.). The volume per drop was in 0.1-1 µL range. The overfilled membrane cocktails covered the periphery of nanopore, and the final structure of the electrode is schematically depicted in FIG. 2d.

TABLE 1

Membrane compositions of the nanopore based all-solid-state potassium-selective electrodes[a]

| Membrane[b] | Matrix c-PVC[c] | Plasticizer DOA[d] | Additives KTFPB[e] | Additives ETH500[f] | Hydrogel PVA[g] | Slope[h] mV/decade |
|---|---|---|---|---|---|---|
| A | 33.0 | 66.0 | | | N | 28.9 |
| B | 33.0 | 65.5 | 0.5 | | N | |
| C | 33.0 | 65.5 | 0.5 | | Y | 22.4 |
| D | 33.0 | 65.5 | | 0.5 | N | 30.1 |
| E | 33.0 | 65.5 | | 0.5 | Y | 44.6 |
| F | 33.0 | 65.0 | 0.5 | 0.5 | N | 27.0 |
| G | 33.0 | 65.0 | 0.5 | 0.5 | Y | 35.7 |

[a]In wt %.
[b]All membranes contain 1 wt % valinomycin.
[c]Carboxylated poly(vinyl chloride).
[d]Bis(2-ethylhexyl)adipate.
[e]Potassium tetrakis[3,5-bis(trifluoromethyl)phenyl]borate.
[f]Tetradodecyl ammonium tetrakis-(p-chlorophenyl)borate.
[g]poly(vinyl alcohol) with $10^{-2}$ M KCl.
[h]Slopes Bom $10^{-5}$M-$10^{-1}$M. N = no and Y = yes.

TABLE 2

Membranes with reduced c-PVC/plasticizer ratios used for the glass nanopore based all-solid-state potassium-selective electrodes[a]

| Membrane[b] | Matrix c-PVC[c] | Plasticizer DOA[d] | Slope[e] mV/decade | Response Time[f] $t_{95}$, sec |
|---|---|---|---|---|
| H | 4.9 | 94.1 | 53.0 | 7.2 |
| I | 9.9 | 89.1 | 53.0 | 6.2 |
| J | 16.5 | 82.5 | 50.4 | 5.2 |
| K | 24.7 | 74.3 | 42.6 | 4.9 |

[a]In wt %.
[b]All membranes contain 1 wt % Valinomycin.
[c]Carboxylated poly(vinyl chloride).
[d]Bis(2-ethylhexyl) adipate.
[e]Slopes from $10^{-5}$ M – $10^{-1}$ M.
[f]Activity change from $10^{-3}$ M – $10^{-2}$ M.

Example 5

Optical Microscopy of Electrode Structure

Figure 3A:
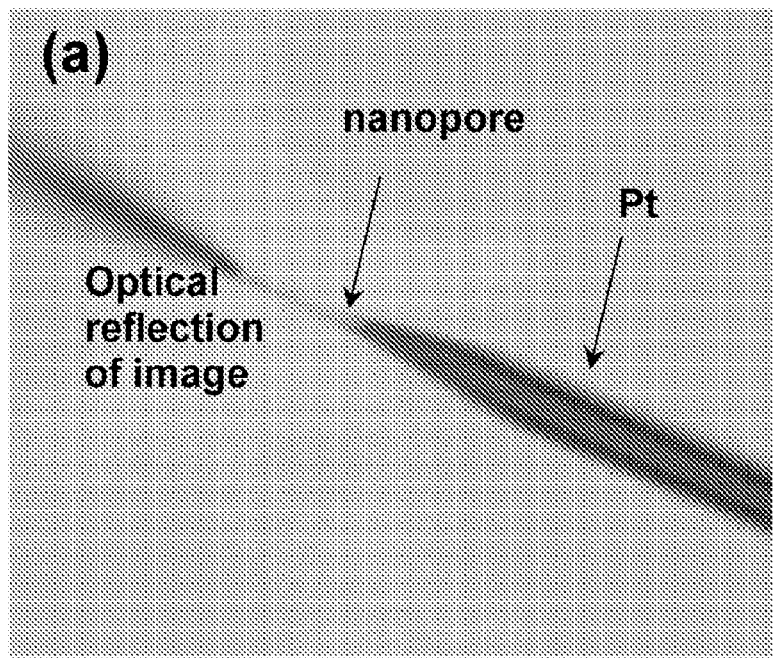
FIG. 3a shows a photograph of a glass nanopore electrode taken with a digital camera through an optical microscope.
Figure 3B:
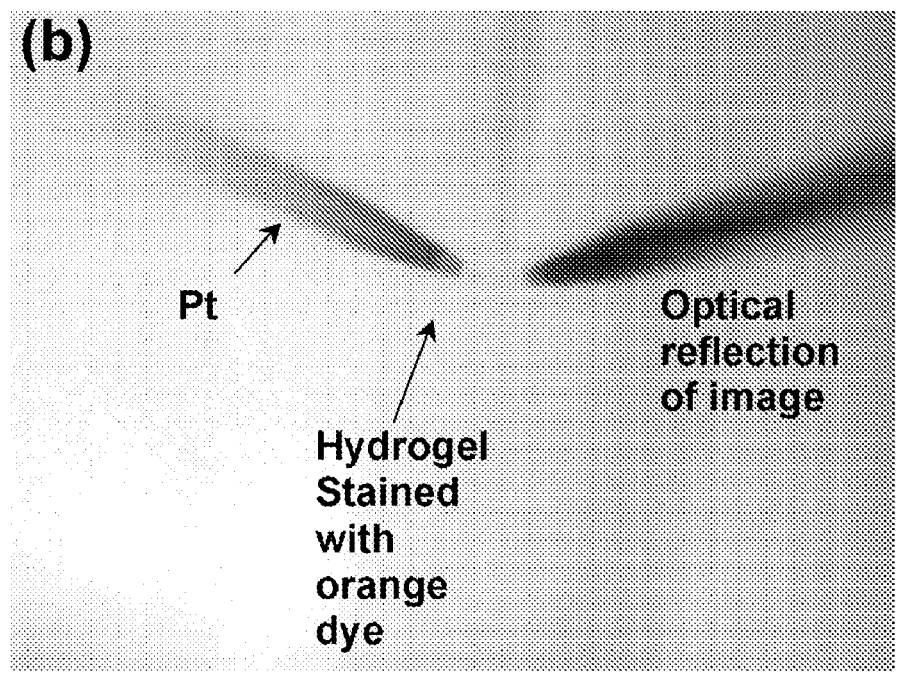
FIG. 3b shows a photograph of a glass nanopore electrode taken with a digital camera through an optical microscope after deposition of a Ag/AgCl layer, hydrogel, and ion selective membrane. A organic dye is dissolved in the hydrogel to allow visualization of this layer.

FIG. 3a shows an optical micrograph of a conical shaped nanopore in glass created by etching a sharpened Pt wire embedded in soda lime glass. FIG. 3b shows an optical micrograph of a conical shaped nanopore in glass created by etching a sharpened Pt wire embedded in soda lime glass, and after partially filling the nanopore with polyvinylalcohol containing a orange dye. Similar microscopic examination of nanopores containing Ag/AgCl and the ion selective membrane confirm the structure schematically depicted in FIG. 1 of a nanopore ion-selective electrode.

Example 6

Potentiometric SECM Imaging

Figure 4:
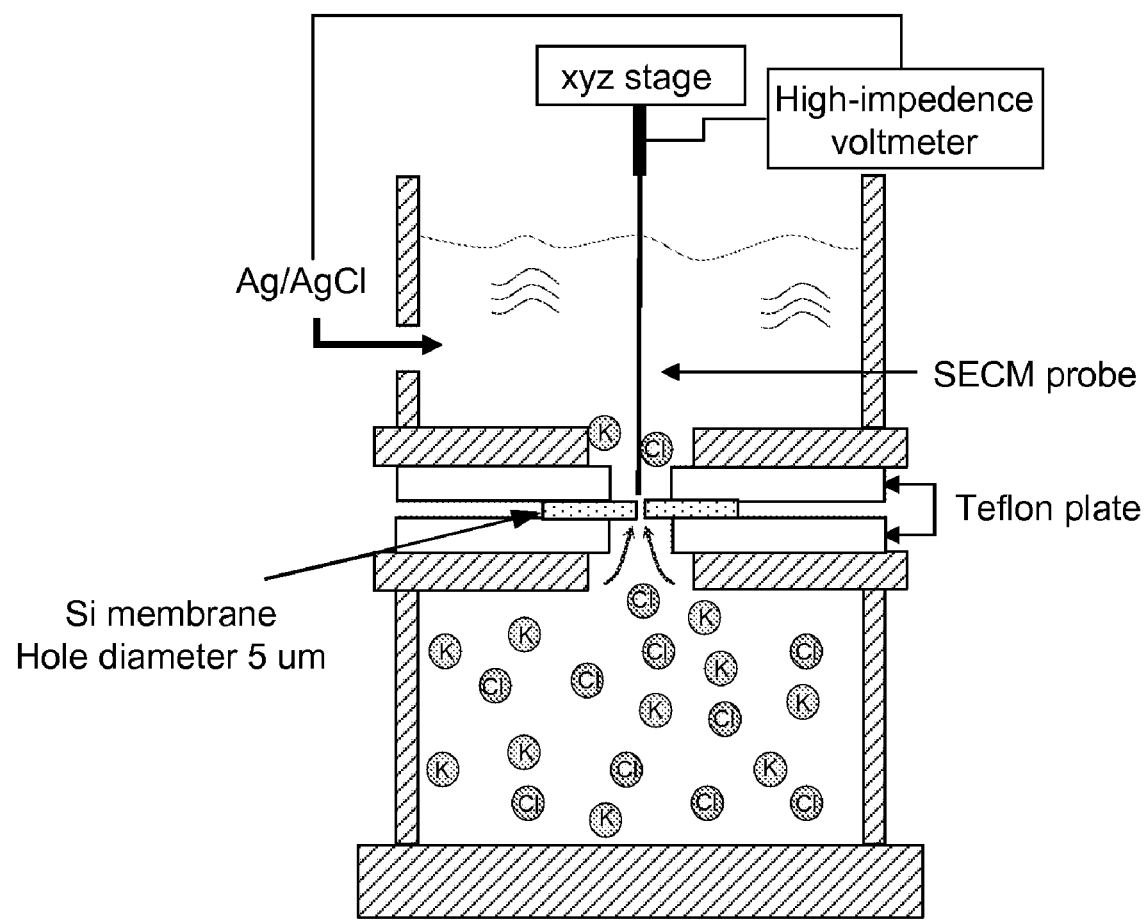
FIG. 4 shows a schematic diagram of a SECM and the cell for potentiometric imaging.

A schematic diagram of the SECM instrumentation used to demonstrate the utility of conical shaped ion-selective electrodes is shown in FIG. 4. Briefly, a Si membrane (thickness <100 μm) containing a 5 μm-diameter hole in the center is sandwiched between two Teflon slides with circular hole. The solutions beneath and above the membrane are 0.1 M KCl and 0.05 M Tris-$H_2SO_4$ (pH 7.4), respectively. The position of the SECM tip (Ag/AgCl-deposited nanopore electrode) is controlled by piezoelectric inchworm microtranslation stages with optical encoding (TSE-75, Burleigh Instruments, Fisher, N.Y.) interfaced via a controller box to LabView. The tip position is controlled at 100 nm precision. The SECM tip is positioned directly over the membrane surface by the reflection of Si surface and by monitoring small potential variation. The z-axis origin is defined by lowering the tip until the tip makes contact with the membrane surface with an accuracy of ~1 μm, and the tip was maintained at about 20 μm above the Si substrate. A home-built low-noise potentiostat is employed to control the potential of the SECM tip with respect to a conventional liquid junction-type reference electrode (Orion model 90-02 sleeve-type double junction Ag/AgCl electrode; internal electrolyte: 3M KCl, and electrolyte in outer jacket: 3 MKNO$_3$). The tip potential was sampled with in house data acquisition programs written in LabView.

Example 7

Measurement of the Electrochemical Radii

Pt nanodisk electrodes were prepared as described in Example 1, and their electrochemical radii were volumetrically determined. Steady-state diffusion-limited currents were measured from the oxidation of 0.005 M Fc in a 0.1 M TBAPF$_6$ supporting electrolyte. Using the equation for the limiting current of UME ($i_{lim}$=4nFDC*a), it was estimated that the radii of Pt nanodisks was in the 1-500 nm range.

Example 8

Preparation and Testing of Glass Nanopore Electrodes

Figure 5:
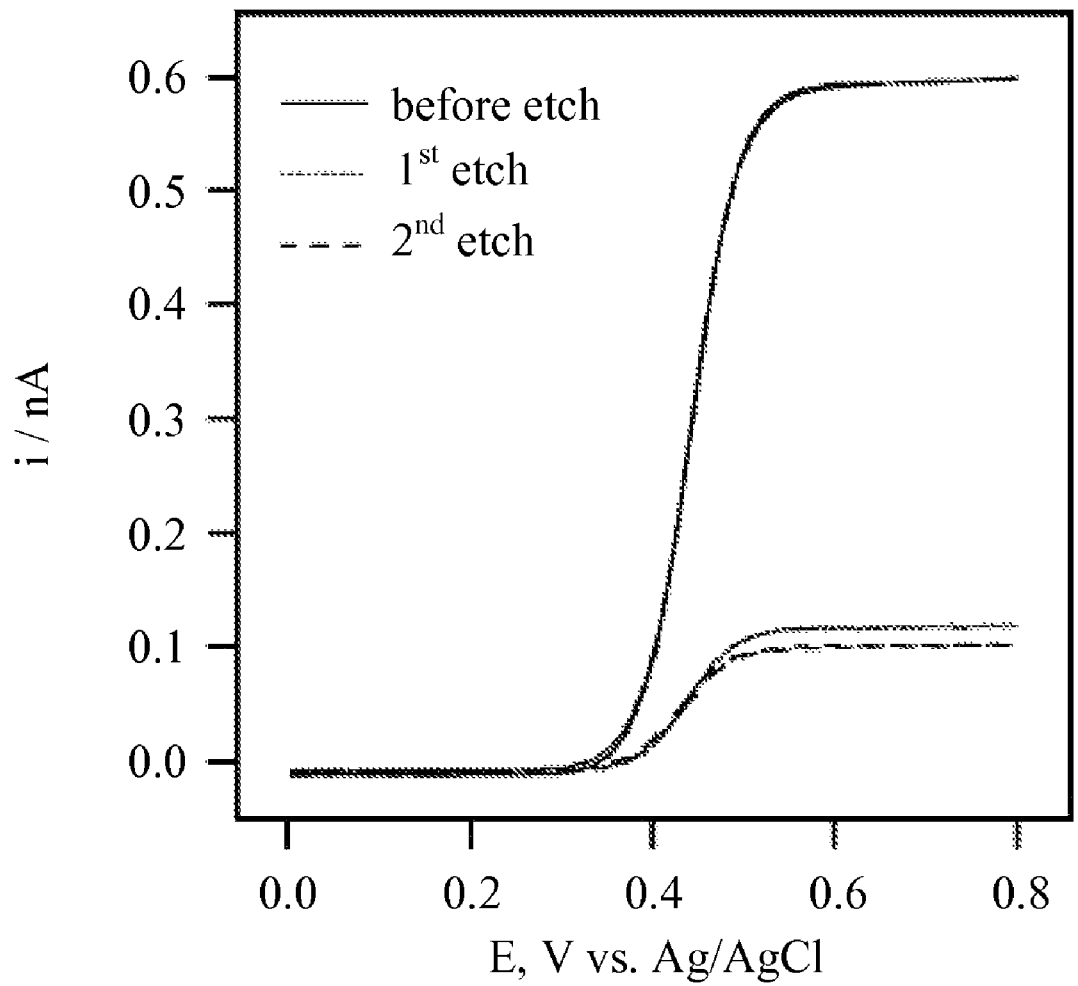
FIG. 5 is a graph depicting the steady-state voltammetric responses of a 132-nm nanodisk Pt electrode in 100 mM $TBAPF_6/CH_3CN$ containing 5 mM Fc (fusicoccin) with scan rate of 100 mV/s before and after etching. The electrochemical etching of the Pt electrode was carried out in a 1.2 M $CaCl_2$ solution (pH 5.5) at 4.5 $V_{ac}$ for 10 s (first etching) or an additional 10 s (second etching).

Glass nanopore electrodes were obtained by electrochemically etching the exposed Pt nanodisk in 1.2 M CaCl$_2$ solution (pH 5.5) at 4.5 VAC (see Experimental). FIG. 5 shows the voltammetric responses of nanodisk and nanopore electrodes in a CH$_3$CN solution containing 5.0 mM Fc and 0.1 M TBAPF6 (tetrabutylammonium hexafluorophosphate). The voltammogram for the nanodisk is sigmoidal shaped and displays very little hysteresis on the reverse scan. From the voltammetric diffusion-limited current, ilim=0.61 nA, the radius of the disk is calculated to be 132 nm. The Pt electrode was then electrochemically etched for 10 s once or twice in a 1.2 M (v/v) CaCl$_2$ solution at 4.5 VAC to create a nanopore electrode. After the etching, voltammograms (FIG. 5) were taken under the same experimental condition to ensure the formation of nanopore electrodes. The depths of the pores were estimated to be deeper than 30 μm. The nanopore electrodes were then used to construct all-solid-state ISEs by modifying the exposed Pt electrode with ion-selective electrode materials.

Example 9

Testing of a Glass Nanopore Based pH Sensor

It is known that IrO$_2$ films deposited onto metal electrodes behave as an excellent pH sensors. However, IrO$_2$ film formation on small Pt electrodes is irreproducible because of the poor adhesion of the film to the Pt surface. The nanopore structure provides an ideal geometry that can contain the deposited IrO$_2$ film, providing mechanical robustness to the device. Since the adhesion of IrO$_2$ film to Pt surface is greatly affected by its cleanliness, the film deposition process was carried out immediately after the nanopore Pt electrode was created to minimize the possibility of ambient chemical contamination. The solution used for electrodeposition is an alkaline iridium (IV) solution containing oxalate, which complexes iridium ions to prevent precipitation at high pH. It is suggested that the IrO$_2$ film is formed by the following reaction at the anode:

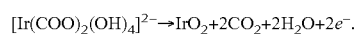

$$[Ir(COO)_2(OH)_4]^{2-} \rightarrow IrO_2 + 2CO_2 + 2H_2O + 2e^-.$$

Figure 6A:
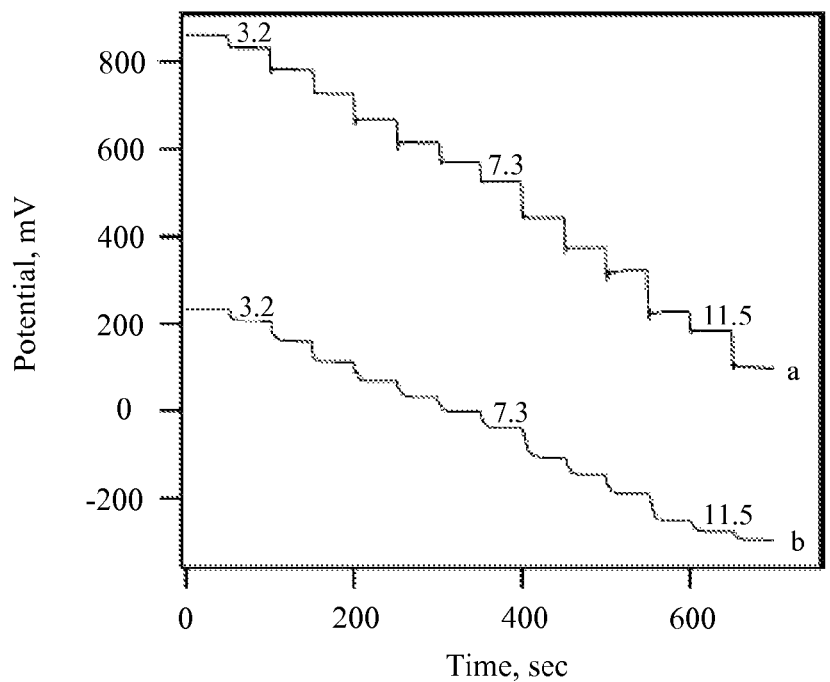
FIGS. 6A and 6B are graphs depicting the potentiometric responses of an $IrO_2$-deposited nanopore electrode (curve a: slope: −79.7 mV/pH) and glass pH electrode (curve b: −58.5 mV/pH) to varying pH: (a) dynamic responses; and (b) calibration plots.
Figure 6B:
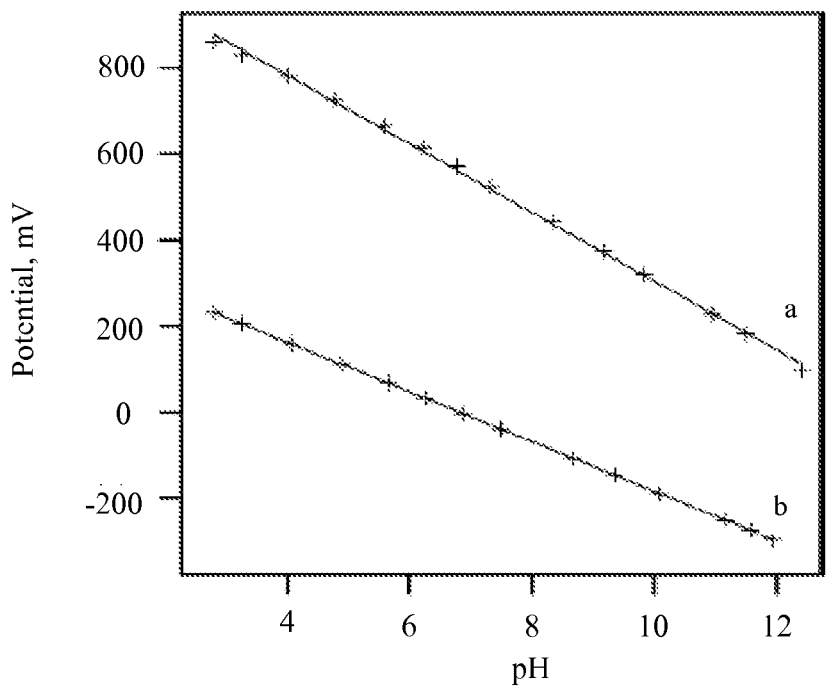

A good quality film at constant current conditions was difficult as the deposited IrO$_2$ quickly form a column-like thread outside the pore. On the other hand, the electrodeposition of IrO$_2$ by cycling the voltage (ten times) at a constant scan rate confined the film to within the pore. From the total integrated current per cycle, 3.8×10$^{-10}$ C, and the density of IrO$_2$ (11.7 g/cm$^3$), the thickness of the deposited film can be estimated; and is in the order of a few nanometers (e.g. 1-5 nm). The potentiometric response of the IrO$_2$-deposited nanopore electrode to pH (between 2 and 10) was measured by adding aliquots of NaOH to universal buffer solutions (11.4 mM boric acid/6.7 mM citric acid/10.0 mM NaH2PO4) at room temperature. For comparison, the response of a commercial glass pH electrode was measured in the same experimental conditions. The significant difference was found in the response slopes of the two electrodes as shown in FIG. 6: −79.7±2.3 mV/pH for the $IrO_2$ nanopore electrode and −58.5±1.0 mV/pH for the glass electrode. The super-Nernstian slopes of $IrO_2$-based pH sensors have been explained based on the stoichiometric ratio of protons and electrons that balance the iridium oxyhydroxide compositions in the iridium oxide film. The $IrO_2$-deposited nanopore electrodes exhibited highly linear and reproducible responses ($R^2$=0.9993) as shown in FIG. 6, and could be used for more than 3 weeks with no degradation of the performance without any protective coating (e.g., Nafion) on the $IrO_2$ film.

Example 10

Preparation and Testing of a Glass Nanopore Based Ag/AgCl Electrode

Figure 7:
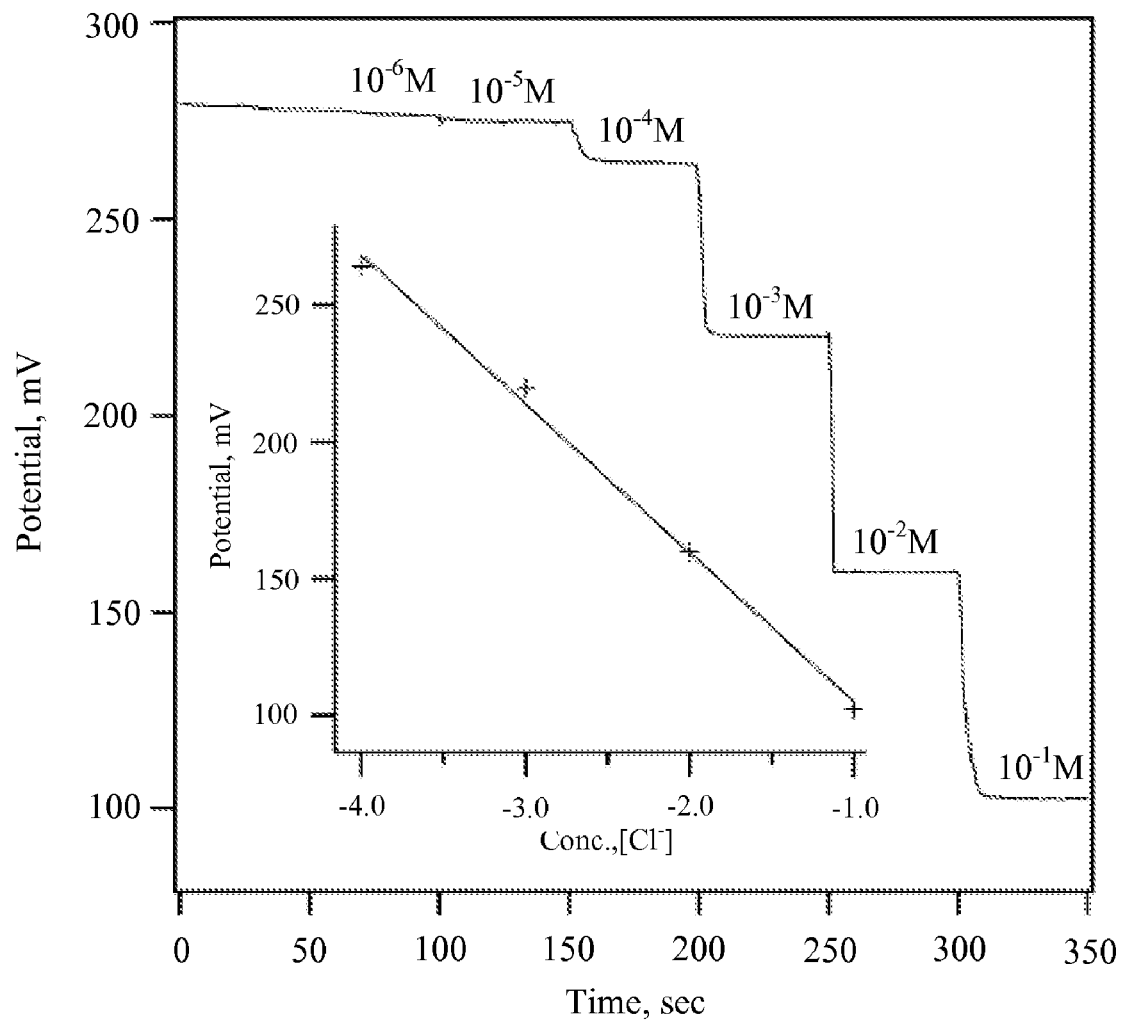
FIG. 7 is a graph depicting the potentiometric response of the Ag/AgCl layer-modified nanopore Pt electrode to $Cl^-$, including an inset of the calibration plot.
Figure 8:
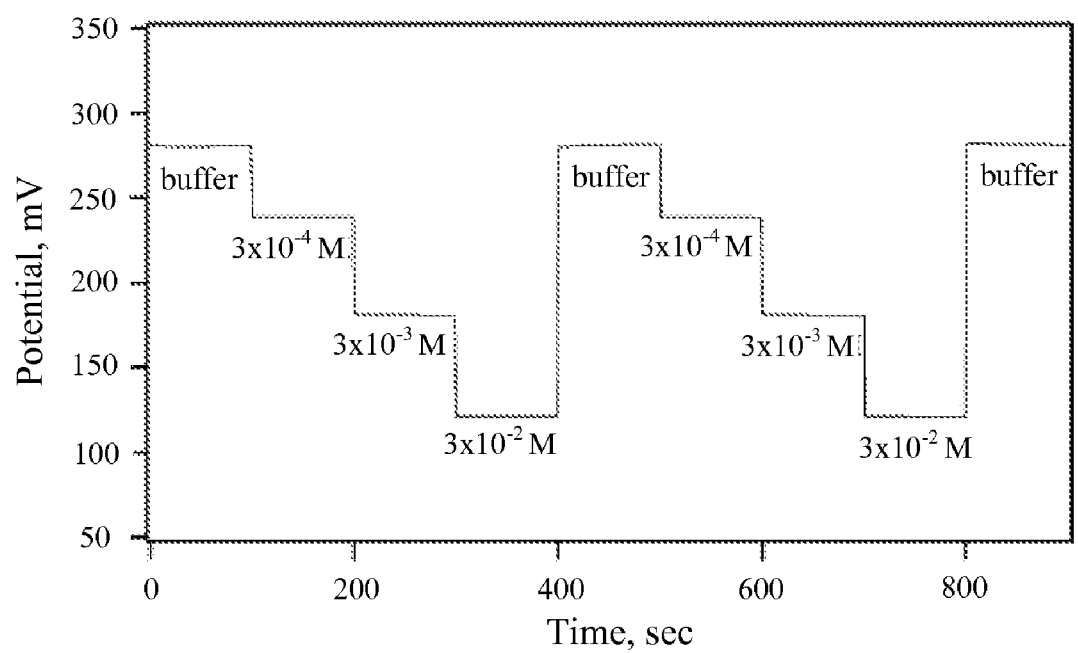
FIG. 8 is a graph depicting the reproducibility of the Ag/AgCl layer-modified nanopore Pt electrode to varying Cl concentrations.

The formation of the Ag/AgCl layer on the nanopore Pt electrode involved a two step process: electrodeposition of a Ag layer on the Pt base electrode, and chloridation of the Ag layer. Direct deposition of the Ag layer in 0.10 M $AgNO_3$, 0.50 M $NH_4OH$, and 0.10 M $NH_4NO_3$ solution does not result in the film formation, because the Ag tends to grow like a column and extends out of the pore forming a lump at the tip. This problem can be avoided by complexing the $Ag^+$ with EDTA (or other suitable silver complexing agent), yielding more controllable deposition conditions. The Ag was deposited in the presence of 0.2 M EDTA at scan rate below 5 mV/s. One cycle (~1.1×10$^{-4}$ C) was sufficient to form a Ag layer within the pore. If the electrodeposition is conducted at a higher scan rate and/or with multiple cycles, lumps of Ag tend to grow out of the pore, failing to form a film within the pore. The thickness of the Ag layer was estimated to be thicker than 25 μm. After the Ag layer is deposited, the nanopore electrode is carefully dipped into a stirred 3 M ferric chloride solution for 30 min. We first examined the potentiometric chloride response of the Ag/AgCl electrode formed in the nanopore (orifice diameter <500 nm). FIG. 7 presents dynamic response toward $Cl^-$. The electrode exhibited a highly linear response ($r^2$=0.996) over the $Cl^-$ concentration from 1.0× 10$^{-4}$ to 1.0×10$^{-1}$ M with a slope of 54.5 mV/p$Cl^-$. The reproducibility of the nanopore Ag/Ag$Cl^-$ electrode was examined by alternating the concentration of $Cl^-$ solution. As shown in FIG. 8, the response of electrodeposited nanopore Ag/AgCl electrode is very fast (<3 s from 10$^{-3}$ to 10$^{-1}$ M), stable, and highly reproducible. The useful lifetime of the nanopore Ag/AgCl electrode was several weeks.

Example 11

Potentiometric SECM Imaging: Measurement of $Cl^-$ Ion Flux

Figure 9A:
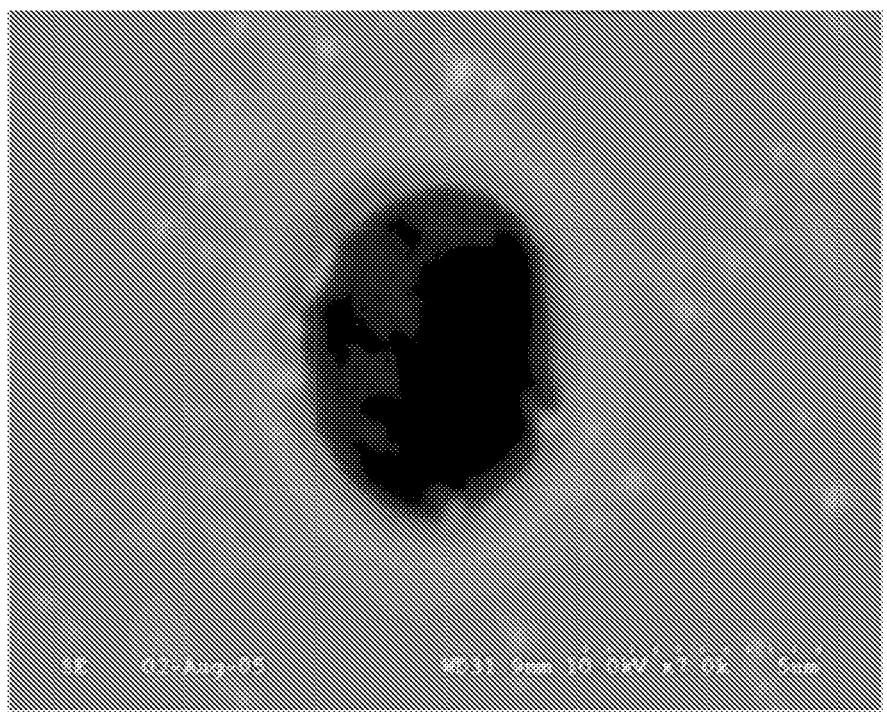
FIG. 9(a) shows an SEM image of a Si membrane with 5 µm diameter hole and FIG. 9(b) shows an SECM image of the chloride ion distribution over a source of 5 µm diameter hole as $Cl^-$ diffuses from the lower compartment (0.1 M KCl) to the upper compartment (0.05M $Tris-H_2SO_4$, pH 7.4). The SECM image was obtained with the Ag/AgCl layer-modified nanopore Pt electrode at a height of ~20 µm above the Si membrane (scan rate, 1 µm/s).
Figure 9B:
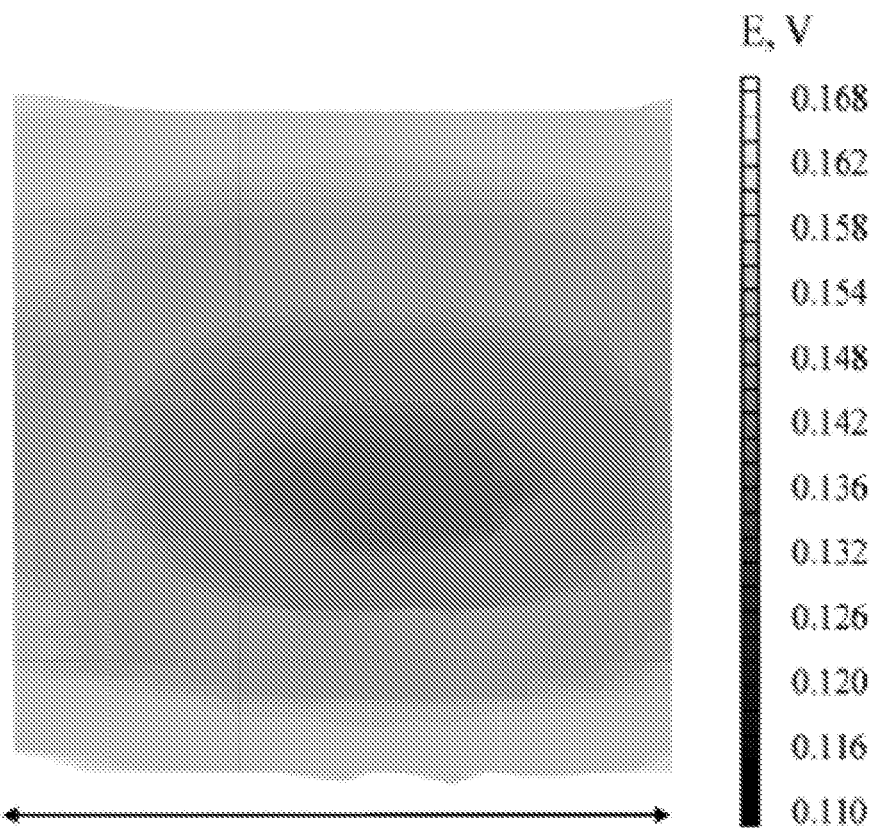

To demonstrate the utility of nanopore-based Ag/AgCl electrode, we imaged the Cl-ion flux through a micrometer size hole (5 μm) in a Si wafer. The cell and SECM instrumentation are schematically depicted in FIG. 2, and the details are described above. The solutions beneath and above the membrane were 0.1 M KCl and 0.05 M tris-$H_2SO_4$ (pH 7.4), respectively. FIG. 9 shows the SEM image of the pore micromachined in Si substrate, and the corresponding SECM image of the Cl-distribution around the pore: the image of the pore and its surroundings are clearly distinguished. The diameter of the ISE image was about 15 μm, which is 3 times larger than the real pore due to the diffusion of $Cl^-$ as it exits the pore. This result demonstrates that the nanopore-based ISEs can be used as a SECM probe.

Example 12

Preparation and Testing of Polymer Membrane-Filled Nanopore Electrodes

Polymer membrane-filled nanopore electrodes were constructed by filling the Ag/AgCl-modified nanopore electrode (orifice diameter: 100~500 nm), which was prepared as described in Example 4. Carboxylated PVC (c-PVC) was used because it exhibits improved adhesion to a solid surface. The polymer to plasticizer ratios are commonly kept at 1:2. The membrane and the base Ag/AgCl electrode in nanopore make a direct contact without the need of internal reference solution used in conventional or micropipette-based ISE; the nanopore based potentiometric electrode of this kind may constitute the smallest all-solid-state ISE known to date.

Figure 10A:
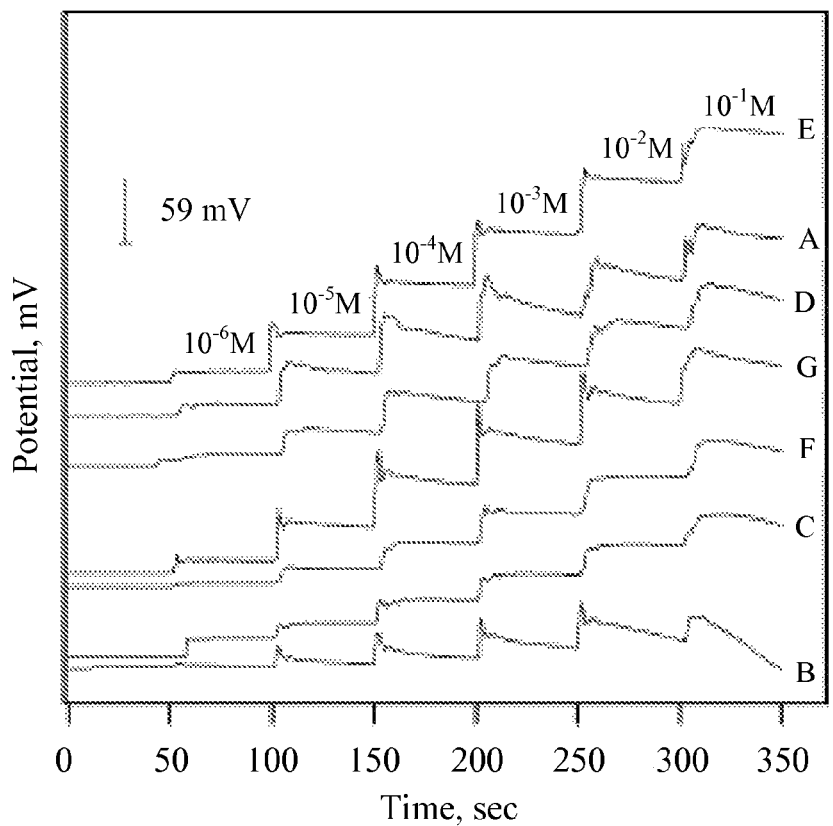
FIG. 10a is a graph depicting the potentiometric responses of glass nanopore (PV/Ag/AgCl) electrodes filled with various valinomycin containing c-PVC-based membranes to $K^+$ concentration. The compositions of the membranes are listed in Table 1.
Figure 10B:
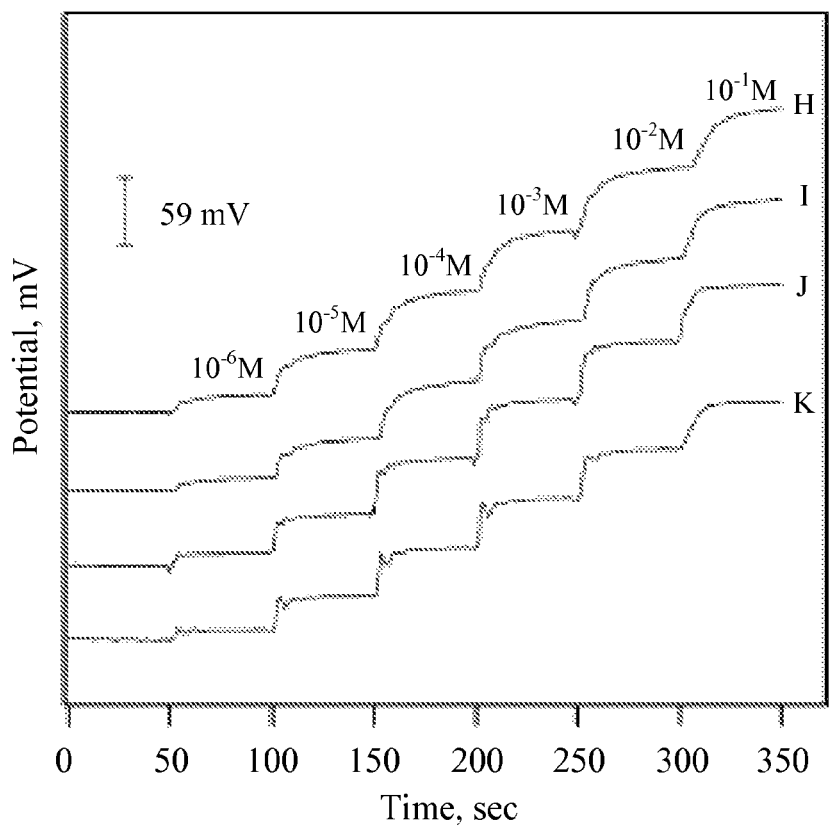
FIG. 10b is a graph depicting the potentiometric responses of glass nanopore (PV/Ag/AgCl) electrodes filled with various valinomycin containing c-PVC-based membranes to $K^+$ concentration. The c-PVC/plasticizer ratios (in wt %) are: (H) 1:19; (I) 1:9; (J) 1:5; (K) 1:3 (see Table 2).

The $K^+$-selective membrane formulated with valinomycin, c-PVC and DOA, membrane A in Table 1, exhibited a transient peak response to the increase of $K^+$ as shown in the dynamic response curve A of FIG. 10. This type of behavior is typically observed in the membranes with high resistance. To lower the membrane resistance while catalyzing the ion-exchange at the membrane surface, a lipophilic additive, KTFPB (potassium tetrakis[3,5-bis(trifluoromethyl)phenyl] borate), was added to the membrane (composition B), but with no improvement in the performance (curve B in FIG. 10). It was thought that the poor point-contact between the membrane and the submicrometer-scale Ag/AgCl layer in the nanopore results in a very high impedance. To improve the contact, a small drop of hydrogel layer (4 wt % PVA in 0.01 M KCl solution) between the Ag/AgCl and the polymer membrane (composition C) was introduced. The layer absorbs water upon soaking and acts as an internal filling solution. As anticipated, the transient peak responses disappeared with the hydrogel-mediated contact (curve C in FIG. 10). However, the slope of the electrode based on C membrane was still too low: 22.4 mV/decade. Generally, 30 mV/decade or greater can be desirable, although lower values may be sufficiently functional for some embodiments.

The nanopore based electrodes with membrane formulations from (D) to (G) were also examined. A highly lipophilic salt ETH5OO (tetradodecylammonium tetrakis(4-chlorophenyl)borate) was added to the membranes with or without KTFPB to reduce the membrane resistance. The best performance was obtained with the electrode (E): slope 44.6 mV/decade (curve E in FIG. 10). These results indicate that the improved contact between the membrane and the base electrode surface and the reduced membrane resistance can be important for fabricating high performance nanopore ISE.

In the fabrication of micropipette-based ISE, the membranes are often formulated only with a plasticizer, i.e., with no polymer thread to reduce the resistance of the membrane. The membranes that fill the nanopore should keep their shape while firmly adhered on the electrode surface. Hence, the membranes were formulated with varying c-PVC/plasticizer ratios (compositions H, I, J and K) as listed in Table 2. The results are summarized in Table 2 and FIG. 10: the membranes with less than 16.5 wt % of c-PVC (H, I and J) exhibited near Nernstian slopes (>50 mV/decade). Another noticeable effect of increased plasticizer ratio was the increase in response times. The increased plasticizer content increases the hydrophobicity of the membrane, and may hinder the ion exchange at the membrane/aqueous solution phase boundary, resulting in a slowed response times. Nanopore ISEs provide a slightly worse potentiometric performance compared to conventional ISEs. However, the sensitivity of the polymer membrane-filled nanopore ISE are sufficient for analytical work, including SECM probing.

Figure 11:
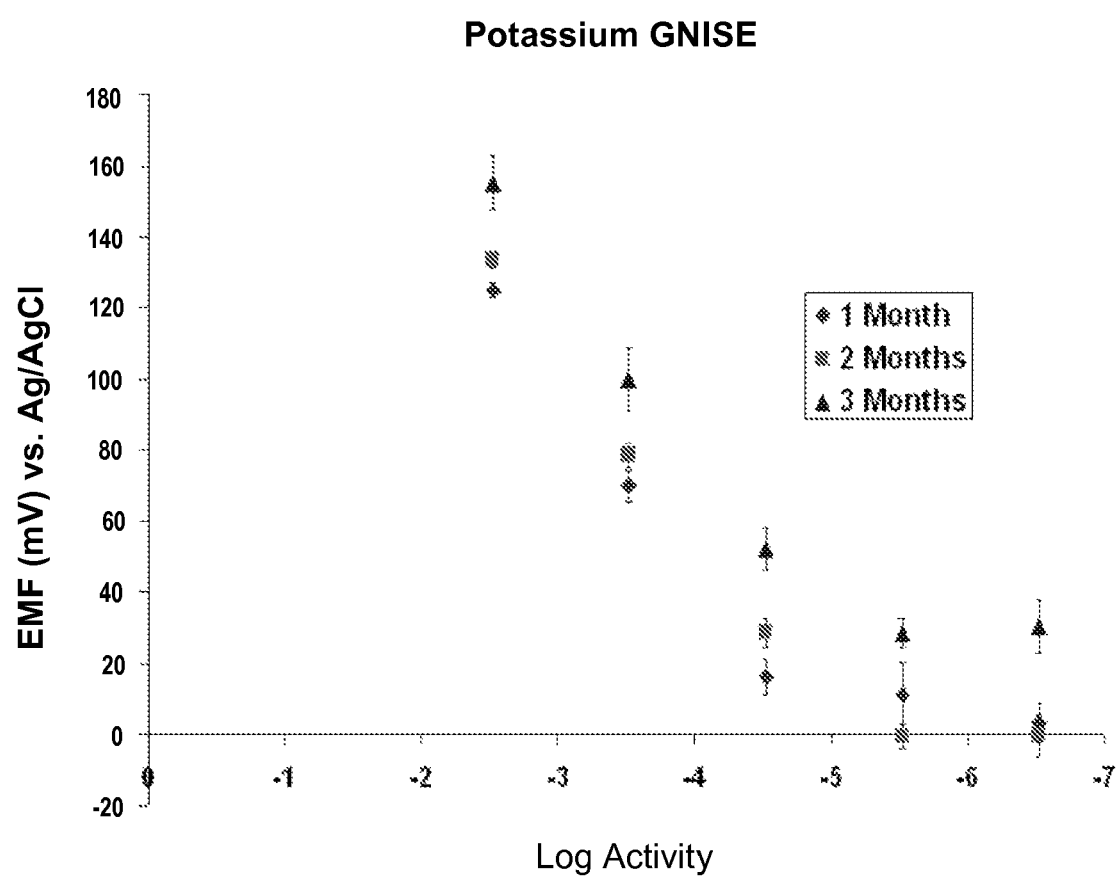
FIG. 11 shows the response of a $K^+$ glass nanopore ion selective electrode over a three month period. The internal volume of the electrode is 0.9 pL. Approximately 4.6 ng of Ag and 600 pg of AgCl were deposited in the pore.

FIG. 11 shows the response of a different $K^+$-glass nanopore ion selective electrode. The data correspond to concentrations of KCl ranging from 0.3 µM to 3 mM, recorded over a period of three months after initial fabrication. The sensitivity is 54 (+/−1.4), 52 (+/−2.4), and 52 (+/−2.1) mV/log $a_K^+$ after 1, 2, and 3 months, respectively. The detection limit of the GNISE is ~30 µM. The ion-selective membrane was composed of (by weight) 1% valinomycin, 9.9% carboxylated PVC, and 89.1% bis(2-ethylhexyl)adipate. Additional $K^+$-selective electrodes have been constructed (not shown) which have a sensitivity of 63 (+/−2.1) mV/log $a_K^+$ and a measuring range between 30 µM and 0.3 M. The detection limits of these electrodes were ~30 µM, and the composition of the ion-selective membranes was 0.5% sodium tetrakis [3,5-bis(trifluoromethyl)phenyl]borate, 1% valinomycin, 9.9% carboxylated PVC, and 88.6% bis(2-ethylhexyl)adipate. The lifetimes of these $K^+$-selective electrodes are several months.

Example 13

$Ca^{2+}$-Nanopore Ion-Selective Electrode

Figure 12:
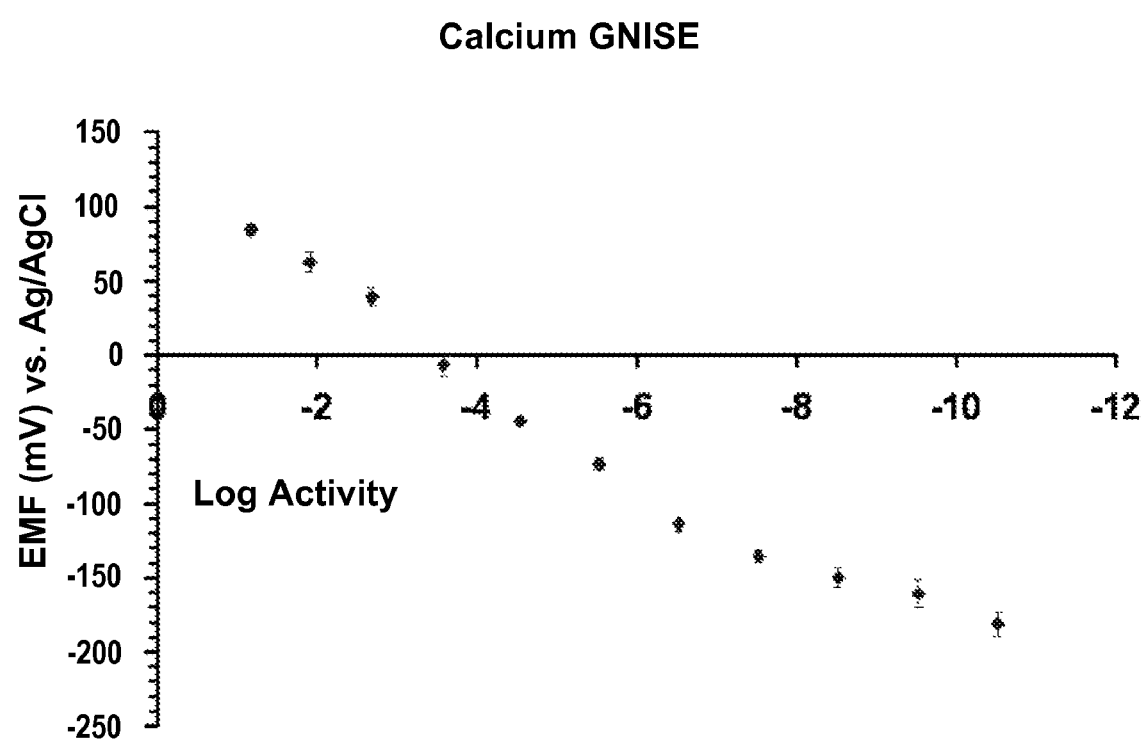
FIG. 12 the response of a $Ca^{2+}$ ion selective electrode. The internal volume of the electrode is 1.2 pL. Approximately 1.9 ng of Ag and 112 pg of AgCl were deposited in the nanopore.

FIG. 12 shows the response of a $Ca^{2+}$-nanopore ion selective electrode to concentrations of $CaCl_2$ ranging from 0.3 nM to 0.3 M. The sensitivity of this electrode is 36 (+/−1.5) mV/log $a_{Ca}^{2+}$, which is super-Nernstian and slightly more sensitive than conventional $Ca^{2+}$-selective ISEs. $Ca^{2+}$-selective nanopore ion selective electrode functioned for approximately one week after initial measurements were taken. The ion-selective membrane was composed of 5% N,N,N',N'-tetra[cyclohexyl]diglycolic acid diamide, 10% carboxylated PVC, and 85% Bis(2-ethylhexyl) adipate.

While the present invention has been described above with particularity and detail in connection with what is presently deemed to be the most practical and preferred embodiments of the invention, it will be apparent to those of ordinary skill in the art that numerous modifications, including, but not limited to, variations in materials, temperature, function, order, and manner of operation may be made without departing from the principles and concepts set forth herein.

What is claimed is:

1. A nanopore based ion-selective electrode, comprising:
   a pore present in a solid material and having a nanosize opening in the solid material;
   an electrical conductor disposed inside the pore opposite the opening in the solid material, wherein said electrical conductor is a microdisk;
   a reference electrode material contacting said electrical conductor and disposed inside said pore;
   a conductive composition in contact with said reference electrode and disposed in said pore; and
   an ion-selective membrane configured to isolate the electrical conductor, reference electrode material, and conductive composition together within said pore.

2. The nanopore based ion-selective electrode of claim 1, wherein the electrical conductor is a Pt micro disk.

3. The nanopore based ion-selective electrode of claim 1, wherein the solid material is selected from the group consisting of glass, polymer, quartz, metal oxide, and combinations thereof.

4. The nanopore based ion-selective electrode of claim 1, wherein the nanosize opening in the solid material is from about 5 nm to about 200 nm in diameter.

5. The nanopore based ion-selective electrode of claim 1, wherein the reference electrode material comprises Ag/AgCl or $IrO_x$.

6. The nanopore based ion-selective electrode of claim 1, wherein the reference electrode material is electrolytically deposited onto the electrical conductor.

7. The nanopore based ion-selective electrode of claim 1, wherein the conductive composition is a conductive solution or hydrogel.

8. The nanopore based ion-selective electrode of claim 1, wherein the ion-selective membrane is deposited at or across the pore opening.

9. The nanopore based ion-selective electrode of claim 1, wherein the pore has a conical shape.

10. The nanopore based ion-selective electrode of claim 1, wherein the nanopore based ion-selective electrode has a diameter of the nanosize opening to pore volume ratio from about 1:10 (nm:µl) to about 1:1000 (nm:µl).

11. An ion-selective electrochemical sensor, comprising: the nanopore ion-selective electrode of claim 1, and a processing unit for processing information from the ion-selective electrode operatively connected to the nanopore ion-selective electrode.

12. The ion-selective electrochemical sensor of claim 11, wherein the ion-selective electrochemical sensor includes an array of two or more nanopore electrodes.

13. The nanopore based ion-selective electrode of claim 1, wherein the ion-selective membrane is located in the pore.

14. A process for producing a nanopore-based all-solid-state ion-selective electrode (ISE), said process comprising:
   a) forming a nanopore within a solid material and having a pore opening and an enclosed volume, wherein a conductive material is oriented opposite the pore opening within the nanopore wherein the conductive material is a microdisk;
   b) forming a reference electrode layer adjacent the conductive material;
   c) forming a conductive composition adjacent the reference electrode layer; and
   d) orienting an ion selective membrane so as to isolate the enclosed volume from fluids external to the nanopore.

15. The process of claim 14, wherein:
   a) the step of forming the nanopore includes sealing a conductive metal wire in the solid material, said solid material being glass or quartz; exposing a disk of said conductive metal wire by gentle grinding; and etching away at least a portion of the conductive metal wire to form the nanopore;
   b) the step of forming the reference electrode layer includes electroplating the exposed disk of the conductive metal within the pore with Ag to form a layer of silver on the exposed disk, and chloridating at least a portion of the Ag layer in order to obtain a AgCl/Ag layer within the pore.

16. The process of claim 15, further comprising adjusting an ion concentration in the conductive composition sufficient to sufficient to prevent the chemical dissolution of the reference electrode.

17. The process of claim 15, wherein the steps of forming are each additive processes.

18. The nanopore based ion-selective electrode of claim 17, wherein the electrical conductor is selected from the group consisting of platinum, copper, silver, gold, tin, lead, conductive polymer, and alloys thereof.

19. The process of claim 15, wherein the conductive metal wire is selected from the group consisting of platinum, copper, silver, gold, tin, lead, and alloys thereof.

20. The process of claim 14, wherein the conductive material is a platinum wire.

21. The process of claim 14, wherein the nanopore has an external opening, said external opening having a diameter of from 5 nm to 200 nm.

22. The process of claim 14, wherein the conductive composition is a hydrogel.

23. The process of claim 14, wherein the nanopore-based all-solid-state ISE exhibits a potentiometric response behavior of about 30 mV/decade to super-Nernstian.

24. The process of claim 23, wherein the ion selective membrane has a plasticizer ratio which is sufficiently low that the potentiometric response behavior is about 40 mV/decade to super-Nernstian.

25. The process of claim 14, wherein the ion-selective membrane is located in the nanopore.

* * * * *